United States Patent
Baker

(10) Patent No.: US 6,825,392 B2
(45) Date of Patent: Nov. 30, 2004

(54) METHOD FOR CONTROLLING NOISOME DECOMPOSITION BYPRODUCTS FROM HUMAN EFFLUX RETAINED IN PERSONAL HYGIENE PRODUCTS

(75) Inventor: Lisa Baker, Lexington, NC (US)

(73) Assignee: Polymer Group, Inc., North Charleston, SC (US)

( * ) Notice: Subject to any disclaimer, the term of this patent is extended or adjusted under 35 U.S.C. 154(b) by 0 days.

(21) Appl. No.: 10/036,902

(22) Filed: Dec. 21, 2001

(65) Prior Publication Data

US 2003/0023212 A1 Jan. 30, 2003

Related U.S. Application Data

(60) Provisional application No. 60/257,227, filed on Dec. 21, 2000.

(51) Int. Cl.[7] .................................. A61F 13/15

(52) U.S. Cl. ................ 604/359; 604/367; 604/360; 604/364; 424/76.1; 424/76.5

(58) Field of Search .................... 604/359, 360, 604/364, 365, 367, 368; 424/76.1–76.4; 428/143, 144, 357, 361; 442/123, 153, 154, 170

(56) References Cited

U.S. PATENT DOCUMENTS

| | | | |
|---|---|---|---|
| 3,506,720 A | | 4/1970 | Model et al. |
| 3,629,477 A | | 12/1971 | Model et al. |
| 4,839,080 A | * | 6/1989 | Jungermann et al. ........ 510/131 |
| 5,710,214 A | * | 1/1998 | Chou et al. .................. 525/124 |
| 5,874,067 A | * | 2/1999 | Lucas et al. ................... 424/65 |
| 5,929,114 A | * | 7/1999 | Domagala et al. ........... 514/562 |
| 5,985,300 A | * | 11/1999 | Crotty et al. ................ 424/402 |
| 6,287,634 B1 | * | 9/2001 | Beall et al. .................. 427/220 |
| 6,348,618 B1 | * | 2/2002 | Anderson et al. ............ 560/174 |

FOREIGN PATENT DOCUMENTS

| | | | | |
|---|---|---|---|---|
| WO | WO99/38541 | * | 8/1999 | ........... A61L/15/46 |

* cited by examiner

Primary Examiner—John J. Calvert
Assistant Examiner—Jacqueline Stephens
(74) Attorney, Agent, or Firm—Wood, Phillips, Katz, Clark & Mortimer

(57) ABSTRACT

The present invention is directed to the control of noisome odors created by the decomposition of human waste in a personal hygiene product. Control of the decomposition process is by the pre-application of an odor control compound comprising a hydroxydiphenyl ether in a modified acidic environment to one or more components of the personal hygiene product. The odor control compound exhibits a multi-functional performance, affecting not only the odiferous decomposition byproducts, but the biochemical decomposition and degradation pathways.

6 Claims, 1 Drawing Sheet

METHOD FOR CONTROLLING NOISOME DECOMPOSITION BYPRODUCTS FROM HUMAN EFFLUX RETAINED IN PERSONAL HYGIENE PRODUCTS

TECHNICAL BACKGROUND

The present invention is generally directed to the control of odors resulting from the decomposition of human efflux, and in particular, the effect of a hydroxydiphenyl ether in a modified acidic environment applied to a personal hygiene product to control odors resulting from autolytic and enzymatic decomposition of human exudates and excreta into volatile nitrogenous byproducts.

BACKGROUND OF THE INVENTION

Disposable absorbent personal hygiene products are designed to capture and retain human excreta in a convenient and in-expensive article. Advances in performance have been made in disposable diapers, adult incontinence pads and feminine hygiene products to further improve waste acquisition and maintain skin wellness. Enhanced top-sheet layers have been introduced that reduce the contact abrasion due to friction of the personal hygiene against one's skin. Transfer intermediate layers are constantly in development whereby the waste, and in particular urine, is quickly wicked from the top-sheet to an absorbent core material. Improved core materials are available that can retain a liquid insult in spite of external compressive forces. While such advances have improved physical performance with regard to liquid and solid wastes, the decomposition of those wastes into volatile byproducts has been addressed with only limited effectiveness.

Disposable diapers and adult incontinence pads have improved in retention capability and can be worn for longer periods without loss of waste containment. While issues related to containment have improved, the development of odors remains a problem.

Urine, a primary form of liquid waste encountered by diapers and incontinence pads, is comprised in significant part of urea. The decomposition of urea results in the formation of volatile nitrogenous byproducts, most notably being ammonia, which are particularly malodorous.

Prior attempts to control ammonia odors have met with limited success. Sequesterants, such as cyclodextrins and zeolite clays are effective only in "capturing" the ammonia once formed. If the structure of the sequesterant becomes occluded or contaminated by the presence of the complex milieu of proteins and salts found in urine, functionality is significantly degraded. The use of acids to shift the pH of the urine insult, and thereby protonate the ammonia into a nonvolatile ammonium ion, has been tried with variable results due, once again, to the chemical complexity inherent to urine. The most practiced method for controlling malodorous decomposition byproducts has been the use of perfumes and fragrances. This practice, however, has generally been found unsatisfactory as ammonia odors are particularly pungent and difficult to mask.

An alternate method by which ammonia odor may be controlled is to target the degradation pathways which produce ammonia.

Autolytic degradation of urea into ammonia occurs when urea is exposed to oxygen. In the environment of a personal hygiene product, and specifically in the fibrous component of a disposable diaper or incontinence pad, urine is wicked into interstices of the product's high loft structure. These interstices form micro-environments where urea autolysis then occurs.

Enzymatic decomposition is an active process induced by specialized enzymes found in bacterial flora. Many genera of bacteria are ubiquitous to the human skin, the gastrointestinal tract, and the uro-genital tract as well as in the form of environmental contaminates found in the personal hygiene products itself. A general category of enzyme present in this flora allows for the breakdown of urea into ammonia. This enzyme is referred in general as a catalase, and specifically as an urease. When there is a liquid insult onto the hygiene product, bacteria are carried along with the liquid front and into the interstices of the fibrous construction. Ureases in the bacterial burden are active during this period, adding significantly to the production of ammonia. Certain bacteria are particularly receptive to this environment and will thrive, blooming the bacterial count and further increasing urea decomposition over time.

Various attempts have been made to control bacterial metabolism and bacterial growth, and thereby reduce odors. As in ammonia protonation, the use of acids as a topical treatment is a relatively effective means for skewing the pH of the environment and imparting a deleterious effect on bacterial health. However, problems in attaining and maintaining a desired pH range against the broad range of urine chemistries encountered in the human population is not trivial. Further, producing a uniform distribution of the acid treatment so as to equally effect all microenvironments is complicated by the solubility of the acid.

There remains an unmet need for an effective treatment for controlling noisome decomposition byproducts, and specifically those byproducts which are ammonia-based, from developing in soiled personal hygiene products. The odor control mechanism must exhibit sufficient robustness in the face of highly variable human waste chemistries while retaining stability during the hygiene product's shelf-life. The present invention addresses these issues through use of a hydroxydiphenyl ether in a modified acidic environment.

SUMMARY OF THE INVENTION

The present invention is directed to the control of noisome odors created by the decomposition of human waste in a personal hygiene product. Control of the decomposition process is by the pre-application of an odor control compound comprising a hydroxydiphenyl ether in a modified acidic environment to one or more components of the personal hygiene product. The odor control compound exhibits a multi-functional performance, affecting not only the odiferous decomposition byproducts, but the biochemical decomposition and degradation pathways.

Human excreta and exudates are received and absorbed into the personal hygiene product. A particularly problematic human waste control issue involves a urine insult in a diaper or incontinence pad. FIG. 1 and FIG. 2 shows typical hygiene product constructions, whereby the urine contacts 10 or 14 a proximal surface of the hygiene product, then wicks through that surface and one or more other dispersing layers, eventually being absorbed into the structure of a 12 lofty fibrous core. Upon leaving the human body and being sequestered into the 12 absorbent core, the constituent chemistry of the urine begins to decompose. Urea, a compound comprising a significant amount of the urine chemistry, decomposes by autolytic and enzymatic mechanisms. The urea is broken down into nitrogenous volatile byproducts, most notably being ammonia. As ammonia evolves out of the solid hygiene product, both malodorous and detrimental skin-wellness effects occur.

By employing the compound of the present invention in one or more layers of the personal hygiene product, the production of ammonia is significantly curtailed. The hydroxydiphenyl ether reduces the metabolic performance of bacteria present in the environment. The presence of the hydroxydiphenyl ether in a modified acidic carrier further improves the bacteriostatic performance of the ether as well as introducing a pH shift that disfavors the further release of ammonia by inducing protonation of the ammonia into a nonvolatile ammonium ion.

The hydroxydiphenyl ether can be present in conjunction with the modified acidic carrier or located within immediate proximity. A preferred embodiment involves the admixing of the hydroxydiphenyl ether with the modified acidic carrier in an aqueous solution. This aqueous solution can then be applied to one or more layers of the personal hygiene product prior to or during product fabrication. Alternately, the hydroxydiphenyl ether can be incorporated into the polymeric composition prior to the formation of that composition into a construct, such as a fiber, filament or film, with the modified acidic carrier being applied topically thereafter. As the hydroxydiphenyl ether blooms to the surface of the construct, interaction with the modified acidic carrier can readily occur.

Other features and advantages of the present invention will become readily apparent from the following detailed description, the accompanying drawings, and the appended claims.

BRIEF DESCRIPTION OF THE DRAWINGS

The invention will be more easily understood by a detailed explanation of the invention, including the drawings. Accordingly, drawings, which are particularly suited for explaining the invention, are attached herewith; however, it should be understood that such drawings are for explanation purposes only and are not necessarily to scale. The drawings are briefly described as follows.

DETAILED DESCRIPTION

Figure 1:
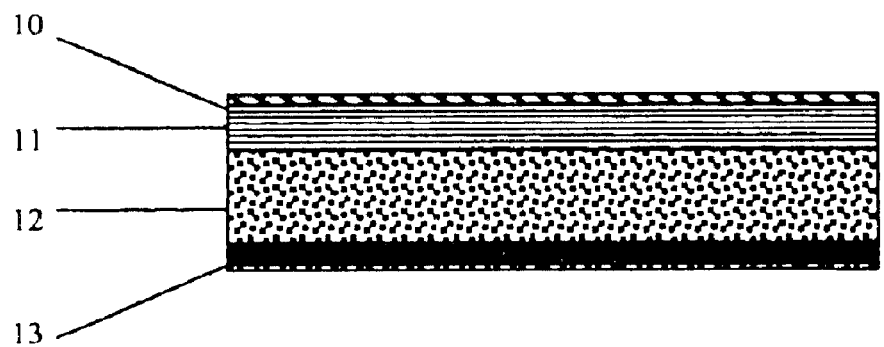
FIG. 1 is a cross-sectional diagram of a typical personal hygiene product.
Figure 2:
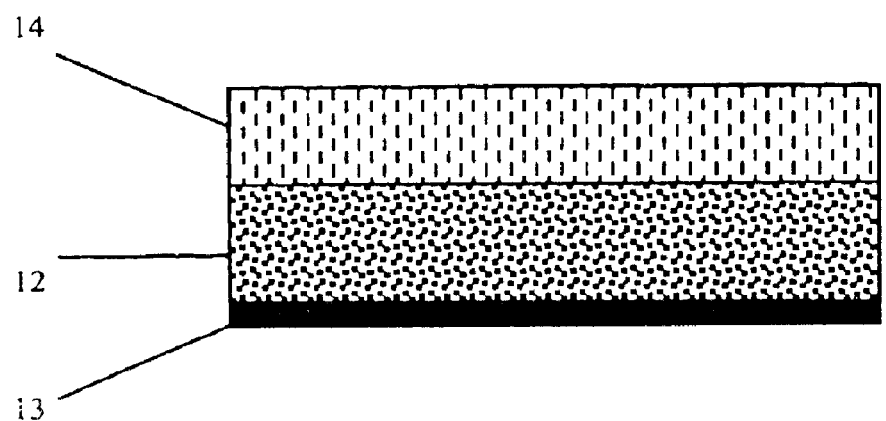
FIG. 2 is a cross-sectional diagram of a modified personal hygiene product having a unified top sheet and transfer layer.

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

To control the production of volatile nitrogenous byproducts, most notably ammonia, produced from the decomposition of urine in a personal hygiene product, a hydroxydiphenyl ether of the following form is used:

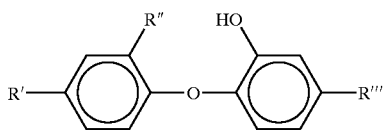

Whereby R', R", and R'", are selected halogen substitutions. A preferred hydroxydiphenyl ether is a trichloro-derivative as described and synthesized in U.S. Pat. Nos. 3,506,720 and 3,629,477, hereby incorporated by reference.

The trichlorodiphenyl ether exhibits bacteriostatic properties in the presence of the bacterial flora found in the personal hygiene product. It is postulated that the reduction of bacterial load reduces the number of viable and metabolically active bacteria, which results in a corresponding decrease in the concentration of catalases found in those bacteria. A reduction in catalase activity, primarily ureases, subsequently reduces the rate at which urea is decomposed into ammonia, and thereby reducing the noisome odors formed in the hygiene product.

By introducing the trichlorodiphenyl ether in a modified acidic carrier, performance of the mixtured is significantly enhanced. Suitable modified acidic carriers include those acids which shift the pH of the trichlorodiphenyl ether environment to an approximate range of between 3.0 and 5.0. It is within the purview of the present invention that either inorganic or organic acids, alone or in combination, can be used in the capacity of a modified acidic carrier. A presently preferred modified acid carrier is one selected from the aliphatic acids, with hexanedioic acid being most preferred.

The hydroxydiphenyl ether and modified acid carrier can be incorporated into a personal hygiene producta, such as a sanitary napkin, diaper, training pant, incontinence pant, and the like, by a number of different routes, including as a topical treatment, a spin finish, and/or a melt additive. Topical treatment is particularly efficacious in incorporating the odor control compound as a simple aqueous solution can be prepared and applied directly to a substrate material, which is then used as one or more component layers in the fabrication of a personal hygiene product. Suitable substrate materials include nonwoven fabrics, woven fabrics, and films.

EXAMPLES

Example 1

A 50 gram per square meter nonwoven fabric was fabricated from carded and thermally bonded staple fiber batt. The staple fiber used was a Type T-187 blue pigmented polypropylene polymer with a 1.5" staple length and a diameter of 12 dpf, as supplied by Fibervisions of Athens, Ga. The staple fiber was carded by conventional practice known to those skilled in the art and subsequently thermal bonded by use of a heated calender. A calender temperature of about 340° F. and a nip pressure of 470 pounds per linear inch were employed.

Example 2

The nonwoven fabric of Example 1 was subsequently treated with an odor control compound comprising 3 mM trichlorodiphenyl ether, supplied as "MICROBAN" from the Microban Corporation, 68 mM hexanedioic acid, and deionized water. A Weko Atomizer was used to uniformly distribute the odor control compound to the nonwoven fabric at an add-on level of 15% by weight.

Table 1 presents the effect of untreated and treated nonwoven fabric on bacterial growth. One inch square samples of Example 1 and Example 2 were placed on uniform bacterial lawns, then incubated overnight. Individually tested bacterial organisms where unable to live under the conditions imposed by the treated nonwoven material whereas the untreated material had no effect.

Table 2 is a variation of the zone of inhibition test performance given in Table 1. A test was performed whereby a bacterial broth receives a one inch sample of either Example 1 or Example 2, then allowed to incubate overnight. When compared to control bacterial broth of known viable organism count, the untreated material is seen to have no significant deleterious effect where as the odor control treated material has reduced viable cell count by at least 95%.

Table 3 provides results on the effectiveness of the odor control compound on perceived odor production. Ten inch by seven inch samples were taken from Example 1 and Example 2. These samples were then substituted for the transfer layer of a "SERENITY" brand adult incontinence pant, a registered trademark of Johnson & Johnson, and a five inch square sample of the entire construct excised from the central medial region of the pant. The construct samples were then transferred to the interior bottom surface of individual glass container. A 100 ml volume of mock urine seeded with bacteria was then applied to the samples and the glass containers closed. At time points throughout the testing perior, the container was briefly opened and the odor compared against the control. As can be seen from the data provided, the perceived smell was significantly reduced.

From the foregoing, it will be observed that numerous modifications and variations can be affected without departing from the true spirit and scope of the novel concept of the present invention. It is to be understood that no limitation with respect to the specific embodiments illustrated herein is intended or should be inferred. The disclosure is intended to cover, by the appended claims, all such modifications as fall within the scope of the claims.

TABLE 1

| Test Material | Zone Of Inhibition (mm) | | |
| --- | --- | --- | --- |
| | Staphylococcus epidermidis | Escherichia coli | Proteus vulgaris |
| Example 1 | 0 | 0 | 0 |
| Example 2 | 9 | 2 | 9 |

TABLE 2

| Test Material | Viability Count | | |
| --- | --- | --- | --- |
| | Staphylococcus epidermidis | Escherichia coli | Proteus vulgaris |
| Example 1 | 100% | 100% | 100% |
| Example 2 | 0.36% | 0.66% | 4.58% |

TABLE 3

| Test Material | Perceived Odor (reduction in odor) | | | | | |
| --- | --- | --- | --- | --- | --- | --- |
| | 1 hr | 2 hr | 4 hr | 6 hr | 8 hr | 12 hr |
| Example 1 | 0% | 0% | 0% | 0% | 0% | 0% |
| Example 2 | 17% | 41% | 18% | 30% | 26% | 42% |

What is claimed is:

1. A composition for controlling odor produced by human waste retained in a disposable hygiene product, comprising an hydroxydiphenyl ether in a modified aliphatic acidic carrier provided on a base substrate material in the form of a dispersing layer of said disposable hygiene product, said base substrate material selected from the group consisting of nonwoven fabrics and polymeric films, said composition being provide by topical application of an aqueous admixture of said hydroxydiphenyl ether an said aliphatic acidic carrier to said substrate, said acidic carrier acting to shift the pH of the hydroxydiphenyl ether environment to an approximate range of between 3.0 and 5.0.

2. A composition for controlling odor as in claim 1, wherein the hydroxydiphenyl ether is a trichlorodiphenyl ether.

3. A composition for controlling odor as in claim 1, wherein the aliphatic acid is a hexanedioic acid.

4. A method for controlling odor produced by human waste retained in a disposable sanitary product, comprising the steps of;

a) providing a base substrate material, b) providing a odor control compound, c) the odor control compound comprising an admixture of a hydroxydiphenyl ether and a modified acid carrier, d) applying the odor control in the form of said admixture compound topically to the base substrate material, e) subsequently forming the treated base substrate material into a dispersing layer for a disposable sanitary product, said acidic carrier acting to shift the pH of the hydroxydiphenyl ether environment to an approximate range of between 3.0 and 5.0.

5. A method for controlling odor as in claim 4, wherein the base material is selected from the group consisting of nonwoven fabrics, woven fabrics, polymeric films, and the combinations thereof.

6. A method for controlling odor produced by human waste retained in a disposable sanitary product, comprising the steps of:

a) providing a base substrate material formed from polymeric composition containing therein a hydroxydiphenyl ether, b) applying a modified acidic carrier to the base substrate material, c) subsequently forming the treated base substrate material into a dispersing layer for a disposable sanitary product, said acidic carrier acting to shift the pH of the hydroxydiphenyl ether environment to an approximate range of between 3.0 and 5.0.

* * * * *